(12) United States Patent
Nguyen et al.

(10) Patent No.: US 11,185,342 B2
(45) Date of Patent: Nov. 30, 2021

(54) RETRIEVAL DEVICES AND RELATED METHODS OF USE

(71) Applicant: Boston Scientific Scimed, Inc., Maple Grove, MN (US)

(72) Inventors: Man M. Nguyen, Harvard, MA (US); Samuel Raybin, Marlborough, MA (US); Tom Bianchi, Hubbardston, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 212 days.

(21) Appl. No.: 16/665,433

(22) Filed: Oct. 28, 2019

(65) Prior Publication Data
US 2020/0060701 A1 Feb. 27, 2020

Related U.S. Application Data

(63) Continuation of application No. 14/846,060, filed on Sep. 4, 2015, now Pat. No. 10,492,808.
(Continued)

(51) Int. Cl.
*A61B 17/221* (2006.01)
*A61B 17/50* (2006.01)

(52) U.S. Cl.
CPC ............ *A61B 17/221* (2013.01); *A61B 17/50* (2013.01); *A61B 2017/2212* (2013.01)

(58) Field of Classification Search
CPC . A61B 17/221; A61B 17/32056; A61B 17/50; A61B 2017/2212; A61B 2017/00358; A61B 2017/00809; A61B 2017/00867; A61B 18/1492; A61B 18/1482; A61B 2018/141; A61B 2018/00267; A61B 2018/00541;
(Continued)

(56) References Cited

U.S. PATENT DOCUMENTS 4,256,113 A   3/1981 Chamness
4,326,530 A   4/1982 Fleury, Jr.
(Continued)

FOREIGN PATENT DOCUMENTS

JP   2001-286479 A   10/2001
WO   2009/055098 A1   4/2008

OTHER PUBLICATIONS

International Search Report and Written Opinion for corresponding PCT Application No. PCT/US2015/048618, dated Oct. 27, 2015, (8 pages).

*Primary Examiner* — Mohamed G Gabr
(74) *Attorney, Agent, or Firm* — Bookoff McAndrews, PLLC

(57) ABSTRACT

According to aspects of the present disclosure, a retrieval device may include a sheath, a first drive member in the sheath, and a second drive member in the sheath. The second drive member may be movable relative to the first drive member. An end effector may be retractable into and extendable out of the sheath. The end effector may include a first proximal end portion coupled to the first drive member, a second proximal end portion coupled to the second drive member, and a plurality of legs extending distally from the first and second proximal end portions to a distal tip of the end effector. All of the legs that extend to the distal tip may be fixed together at the distal tip.

20 Claims, 2 Drawing Sheets

Related U.S. Application Data

(60) Provisional application No. 62/047,250, filed on Sep. 8, 2014.

(58) Field of Classification Search
CPC .......... A61B 2018/00577; A61B 2018/00601; A61B 90/03; A61F 2007/0001; A61F 2007/126; A61F 7/001
See application file for complete search history.

(56) References Cited

U.S. PATENT DOCUMENTS

| | | |
|---|---|---|
| 5,064,428 A | 11/1991 | Cope et al. |
| 5,254,088 A | 10/1993 | Lundquist et al. |
| 6,214,002 B1 * | 4/2001 | Fleischman ........ A61B 18/1492 600/374 |
| 6,348,056 B1 | 2/2002 | Bates et al. |
| 6,656,191 B2 | 12/2003 | Ouchi |
| 7,875,038 B2 | 1/2011 | Que et al. |
| 8,361,084 B2 | 1/2013 | Cheng et al. |
| 2003/0109889 A1 | 6/2003 | Mercereau et al. |
| 2004/0138677 A1 | 7/2004 | Little et al. |
| 2004/0199200 A1 | 10/2004 | Teague et al. |
| 2006/0100544 A1 | 5/2006 | Ayala et al. |
| 2007/0016225 A1 | 1/2007 | Nakao |

* cited by examiner

RETRIEVAL DEVICES AND RELATED METHODS OF USE

CROSS-REFERENCE TO RELATED APPLICATIONS

This application is a continuation of U.S. application Ser. No. 14/846,060, filed Sep. 4, 2015, which claims the benefit of U.S. Provisional Application No. 62/047,250, filed Sep. 8, 2014, the disclosures of which are incorporated herein by reference in their entireties.

TECHNICAL FIELD

Various aspects of the present disclosure relate generally to retrieval devices for retrieving material in a subject's body. More specifically, the present disclosure relates to retrieval devices configured to change shape to facilitate capturing and/or releasing material, and related methods.

BACKGROUND

Retrieval devices may be used to remove material from within a subject's body. The material may include inorganic material, such as parts of a medical device or other foreign matter. The material may also include organic material, such as blood clots, tissue, or biological concretions such as urinary, biliary, and pancreatic stones. Biological concretions can develop in certain parts of the body, such as in the kidneys, pancreas, ureter, and gallbladder.

With conventional retrieval devices, in some instances material may be difficult for a user to capture with the device. For example, the material may be too large to fit through openings in the device. Or the material may be so small that it may slip through the openings in the device. It may also be difficult to keep material in the device when the user attempts to withdraw the material from the subject's body. For example, the material may be too large to be removed intact from a subject's body after it has been captured within the device. To release the material from the device, a user may attempt to dislodge the material from the device by maneuvering the device. If the material cannot be released from the device in that manner, the user may attempt to break the material into smaller pieces in the device using an emergency rescue handle. If the material doesn't break, the device may break along its drive wire. The subject may have to undergo surgery to have the broken device removed.

SUMMARY

Aspects of the present disclosure relate to, among other things, retrieval devices and related methods of use. Each of the retrieval devices and methods of the present disclosure may include one or more of the aspects described in connection with any of the other retrieval devices and methods.

According to aspects of the present disclosure, a retrieval device may include a sheath, a first drive member in the sheath, and a second drive member in the sheath. The second drive member may be movable relative to the first drive member. An end effector may be retractable into and extendable out of the sheath. The end effector may include a first proximal end portion coupled to the first drive member, a second proximal end portion coupled to the second drive member, and a plurality of legs extending distally from the first and second proximal end portions to a distal tip of the end effector. All of the legs that extend to the distal tip may be fixed together at the distal tip.

In addition or alternatively, the device may include one or more of the following features: the retrieval device may include only two drive members; one of the first and second drive members may be movable in at least one of a proximal direction and a distal direction relative to the other of the first and second drive members; one of the first and second drive members may be movable in at least one of a proximal direction and a distal direction while the other of the first and second drive members may not move in the proximal direction or the distal direction; one of the first and second drive members may be movable in a proximal direction while the other of the first and second drive members may be movable in a distal direction; the first and second drive members may be simultaneously movable in at least one of a proximal direction and a distal direction; the distal tip may include a coupler configured to receive the distal ends of the legs; a greater number of legs may extend between the coupler and the first end portion than between the coupler and the second end portion; and/or the distal tip may be movable to a position proximal of at least a portion of the end effector when one of the first drive member and the second drive member is pulled proximally relative to the other of the first and second drive members.

According to aspects of the present disclosure, a retrieval device may include a sheath, and a drive member assembly. The drive assembly may include a first drive member in the sheath, and a second drive member in the sheath. The first drive member may be movable relative to the second drive member. The retrieval device may also include an end effector coupled to the first and second drive members. The end effector may include a plurality of legs. The drive member assembly and the plurality of legs may form a loop. One of the first and second drive members may be configured to form a distal portion of the loop. The distal portion may be extendable out of the sheath while the plurality of legs are contained in the sheath.

In addition or alternatively, the device may include one or more of the following features: the first and second drive members and the end effector may form a continuous loop; the drive member assembly may include an actuator coupled to the first and second drive members; the actuator may be configured to rotate to move one of the first and second drive members relative to the other of the first and second drive members; moving the first drive member relative to the second drive member may extends the end effector out of the sheath; and/or the actuator may be configured to move in one of a proximal direction and a distal direction to move the first and second drive members in the same direction.

According to aspects of the present disclosure, a method of manipulating material may include deploying an end effector from a distal end of a sheath. The end effector may include a first end portion coupled to a first drive member extending through the sheath, a second end portion coupled to a second drive member extending through the sheath, and an intermediate portion connected between the first and second end portions. The intermediate portion may include a plurality of legs forming a distal end of the deployed end effector. The method may also include maneuvering the deployed end effector around material. Maneuvering may include moving one of the first and second drive members relative to the other of the first and second drive members to move the distal end of the deployed end effector proximal to at least one of the legs.

In addition or alternatively, the method may include one or more of the following features: distal ends of the legs may be joined by a coupler, the coupler forming a distal tip of the deployed end effector, and moving one of the first and second drive members relative to the other of the first and second drive members may move the coupler proximal to at least one of the legs; exerting a compressive holding force on the material with the plurality of legs; the end effector may include a first area with adjacent legs spaced apart by a first distance, and a second area with adjacent legs spaced apart by a second distance greater than the first distance; and/or moving one of the first and second drive members relative to the other of the first and second drive members moves the first area distally and the second area proximally.

It may be understood that both the foregoing general description and the following detailed description are exemplary and explanatory only and are not restrictive of the claimed features.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

Overview

The present disclosure is drawn to retrieval devices and methods where portions of end effector assemblies may change shape to facilitate the capture and release of material. A user may change the shape of a portion of an end effector assembly by manipulating one or more of a plurality of drive members. Reference will now be made in detail to aspects of the present disclosure, examples of which are illustrated in the accompanying drawings. Wherever possible, the same reference numbers will be used throughout the drawings to refer to the same or like parts. The term "distal" refers to a portion farthest away from a user when introducing a device into a subject. By contrast, the term "proximal" refers to a portion closest to the user when placing the device into the subject.

Exemplary Aspects

Figure 1A:
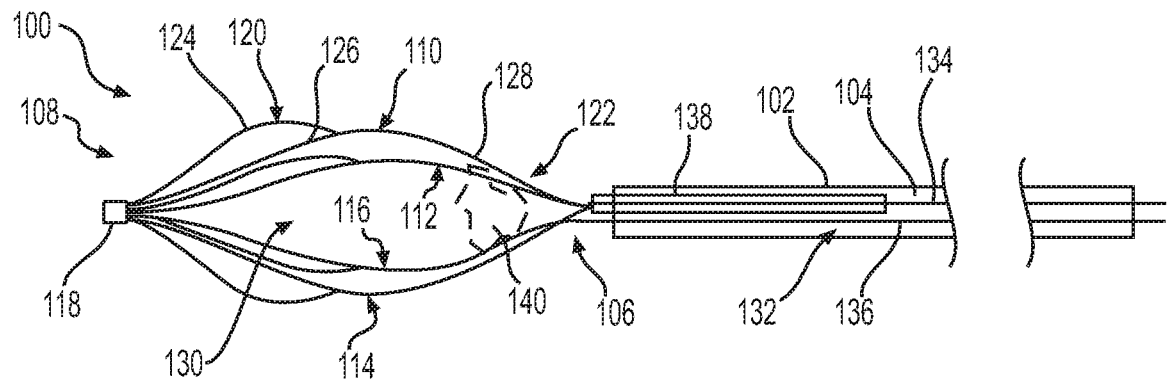
FIG. 1A illustrates portions of an exemplary retrieval device, with an end effector assembly of the device in a deployed state, according to an aspect of the present disclosure.
Figure 1B:
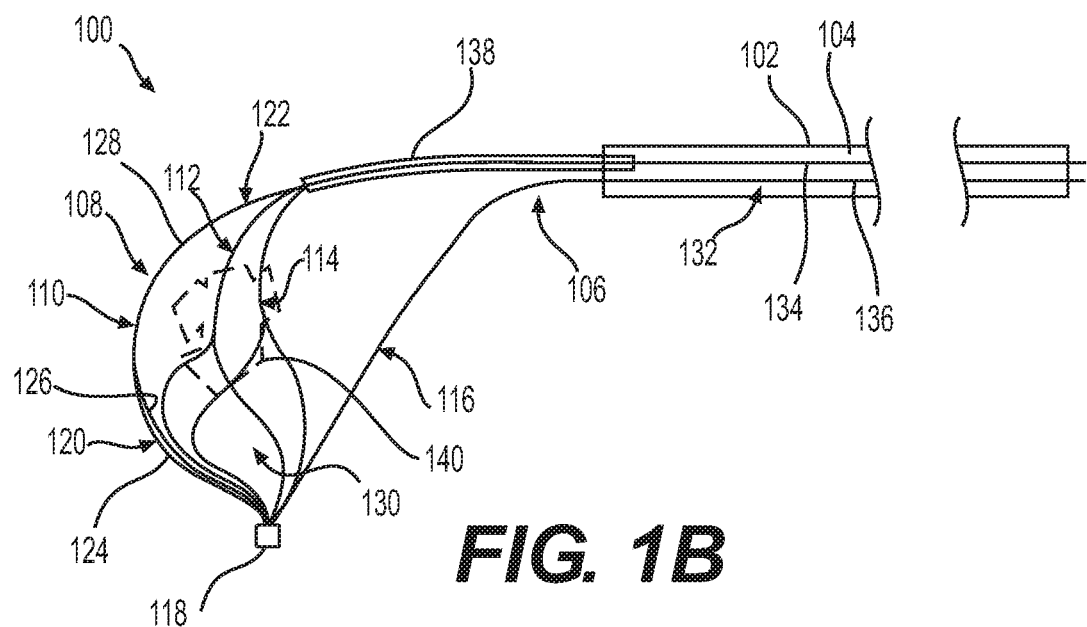
FIG. 1B illustrates portions of the retrieval device of FIG. 1A, with the end effector assembly in a capturing state, according to an aspect of the present disclosure.
Figure 1C:
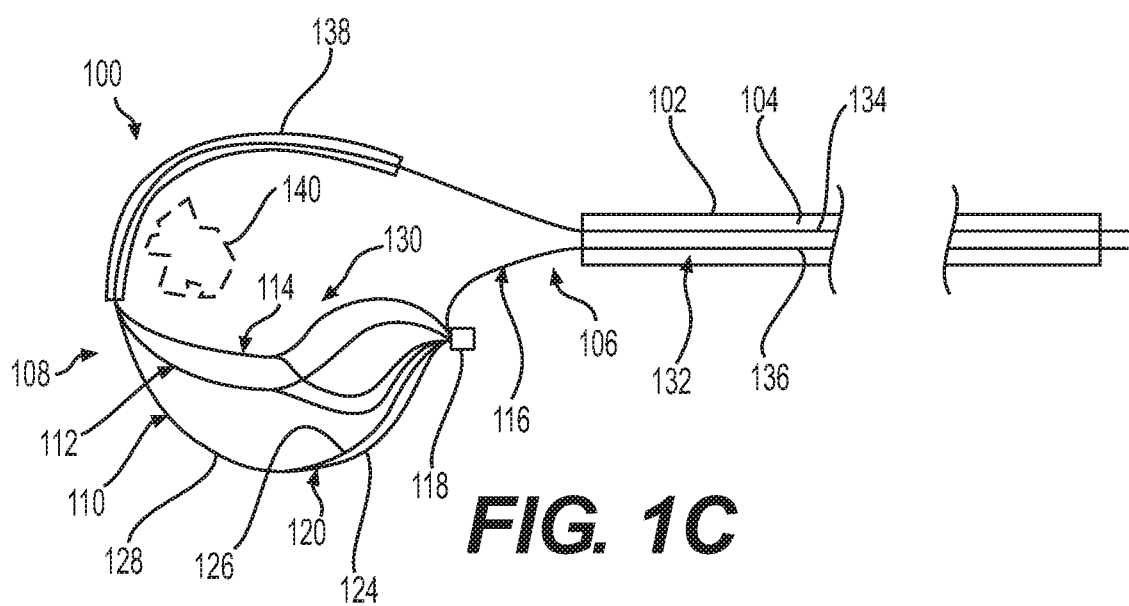
FIG. 1C illustrates portions of the retrieval device of FIG. 1A, with the end effector assembly in a releasing state, according to an aspect of the present disclosure.

FIGS. 1A-1C illustrate an exemplary retrieval device 100. Retrieval device 100 may include an introducer 102. Introducer 102 may include a tubular member, such as a sheath or catheter. Introducer 102 may be made of a flexible material so that introducer 102 can bend when being inserted into and/or navigated through tortuous passages in a subject's body. Introducer 102 may include a lumen 104. It is also contemplated that introducer 102 may include a plurality of longitudinally-extending and/or parallel lumens extending therethrough.

An end effector assembly 106 may be received in lumen 104. End effector assembly 106 may include an end effector 108 configured to capture material. End effector 108 may include a plurality of legs 110, 112, 114, and 116. It should be understood that any suitable number of legs may be used. Legs 110, 112, 114, and 116 may form a basket. The plurality of legs 110, 112, 114, and 116 may extend distally to a distal tip of end effector 108. Legs 110, 112, 114, and 116 may be coupled at their distal ends by an end cap or coupler 118. End cap 118 may be crimped, welded, soldered, or attached in any other suitable way to the distal ends of legs 110, 112, 114, and 116. All of the legs that extend to the distal tip of end effector 108 may be fixed together at the distal tip.

Leg 110 may include a distal section 120, and a proximal section 122. Distal section 120 and proximal section 122 may include one or more struts 124, 126, and 128. Distal section 120 may include a greater number of struts than proximal section 122. For example, distal section 120 may include two struts 124 and 126. Proximal section 122 may include one strut 128. Leg 110 may include, for example, two wires. The two wires may be coupled to form strut 128, and may be uncoupled such that one wire forms strut 124 and the other wire forms strut 126 It should be understood that any suitable number of struts may be used. Legs 112, 114, and 116 may be similar in structure to leg 110.

Legs 110, 112, 114, and 116 may be radially arranged about a central longitudinal axis. The central longitudinal axis may be coaxial with a central longitudinal axis of lumen 104. It is contemplated that legs 110, 112, 114, and 116 may be equally spaced from the central longitudinal axis, and/or equally spaced from each other. Legs 110, 112, 114, and 116 may form an interior region 130 in which material may be captured.

End effector 108 may be retracted into lumen 104 of introducer 102, with end effector 108 contained within lumen 104 and end cap 118 adjacent the distal end of introducer 102. End effector 108 may be extended distally out of the distal end of introducer 102 and lumen 104. When extended, end effector 108 may move into a deployed state (FIG. 1A). End effector 108 may expand as it moves to the deployed state. Legs 110, 112, 114, and 116 may move radially outwardly away from the central longitudinal axis. The size of the gaps between legs 110, 112, 114, and 116 may increase, facilitating entry of material into interior region 130. Legs 110, 112, 114, and 116 may be formed of any suitable material including, but not limited to, metals, polymers, or a combination of materials. For example, one or more of legs 110, 112, 114, and 116 may be formed with a shape memory material, such as Nitinol or stainless steel, and may be treated to possess an internal bias causing one or more of legs 110, 112, 114, and 116 to move radially outwardly away from the central longitudinal axis in the absence of a constraining force.

End effector 108 may be retracted proximally into the distal end of introducer 102. When retracted, end effector 108 may enter a stored state (not shown). End effector 108 may contract as it moves to the stored state. Legs 110, 112, 114, and 116 may move radially inwardly toward the central longitudinal axis. Gaps between legs 110, 112, 114, and 116 may decrease.

End effector assembly 106 may be coupled to an actuation assembly 132 for moving end effector 108 between the stored and deployed states. Actuation assembly 132 may include a plurality of drive members 134 and 136. It is contemplated that any suitable number of drive members may be used. For example, only two drive members may be used. Alternatively, three or more drive members (not shown) may be used. Drive members 134 and 136 may include, for example, one or more wires or cables. Drive members 134 and 136 may extend through lumen 104. It is also contemplated that each of drive members 134 and 136 may extend through its own separate lumen when introducer 102 includes a plurality of lumens.

Proximal end portions of legs 110, 112, and 114 may be coupled to the distal end of drive member 134. For example, proximal end portions of legs 110, 112, and 114 may be welded or soldered to the distal end of drive member 134, joined by a crimp tube (not shown), and/or attached by any other suitable attachment mechanism. The joint between proximal end portions of legs 110, 112, and 114 and the distal end of drive member 134 may be located where legs 110, 112, and 114 meet at the proximal end of end effector 108.

Alternatively, proximal end portions of legs 110, 112, and 114 may be joined by a coupler 138. Coupler 138 may include, for example, a sheath or tube. Legs 110, 112, and 114 may extend proximally through coupler 138. Coupler 138 may be joined to legs 110, 112, and 114 by friction fit, adhesive coupling, heat shrinking, and/or any other suitable form of attachment. Coupler 138 may be flexible enough to be bent by forces exerted on coupler 138 by legs 110, 112, and 114. Within coupler 138, or proximal to the proximal end of coupler 138, proximal end portions of legs 110, 112, and 114 may be coupled to the distal end of drive member 134.

The proximal end portion of leg 116 may be coupled to a distal end of drive member 136. For example, the proximal end portion of leg 116 may be welded or soldered to the distal end of drive member 136, joined by a crimp tube (not shown), and/or attached by any other suitable attachment mechanism. The joint between the proximal end portion of leg 116 and the distal end of drive member 136 may be located at the proximal end of end effector 108. Alternatively, the proximal end portion of leg 116 may form at least the distal portion of drive member 136, or all of drive member 136. It is also contemplated that legs 110 and 112 may be joined by coupler 138 at the distal end of drive member 134, while legs 114 and 116 may be joined by a similar coupler at the distal end of drive member 136.

Drive members 134 and 136 may be moved at the same time. Drive members 134 and 136 may also be moved one at a time. Drive members 134 and 136 may be moved in the same direction. Drive members 134 and 136 may also be moved in different directions. Any combination of the above movements may be executed by a user to perform a procedure. Combinations of the above movements may cause end effector 108, drive member 134, and/or drive member 136 to change shape, thereby facilitating the capture and/or release of material.

Drive members 134 and 136 may be moved at the same time in the distal direction to move end effector 108 from the stored state (not shown) to the deployed state (FIG. 1A). Drive members 134 and 136 may be moved at the same time in the proximal direction to move end effector 108 from the deployed state to the stored state. If material is in the interior region 130, drive members 134 and 136 may be moved in the proximal direction at the same time to grasp the material with legs 110, 112, 114, and 116.

With end effector 108 in the deployed state, material 140 may enter interior region 130. For example, material 140 may pass through one or more of the gaps between legs 110, 112, 114, and 116. A user may maneuver end effector 108 around material 140 to facilitate its entry. The user may, for example, force one or more of legs 110, 112, 114, and 116 against material 140 to squeeze material 140 between legs 110, 112, 114, and 116 and into interior region 130.

At times, the user may have difficulty getting material 140 into interior region 130 with end effector 108 in the deployed state shown in FIG. 1A. The difficulty may be due to the dimensions, shape, and/or location of material 140. The user may move drive member 134 in the distal direction, while keeping drive member 136 still, moving drive member 136 in the distal direction at a slower rate than drive member 134, or moving drive member 134 in the distal direction while moving drive member 136 in the proximal direction. End effector 108 may change shape from the deployed state shown in FIG. 1A to the capturing state shown in FIG. 1B.

To achieve the capturing state of FIG. 1B, the side of end effector 108 having legs 110, 112, and 114 may move distally relative to the side of end effector 108 having leg 116. Legs 110, 112, and 114 may become more bent or curved. Legs 110, 112, and 114 may give that side of end effector 108 a bowl or scoop shape. Legs 110, 112, and 114 may define the distal end of end effector 108 as portions of legs 110, 112, and 114 may move distally relative to end cap 118. Portions of legs 110, 112, and 114 may bulge distally beyond end cap 118. Other portions of legs 110, 112, and 114 may be proximal of end cap 118. It is also contemplated that the size of the gaps between legs 110, 112, and 114 may decrease.

Leg 116 may become less bent or curved. The separation between the side of end effector 108 having legs 110, 112, and 114, and the side of end effector 108 having leg 116, may increase. For example, the size of the gaps between leg 116 and the legs 112 and 114 adjacent to leg 116, may increase. It may be easier for the user to move material 140 into interior region 130 through the gaps on each side of leg 116, due to their increased size. Once material 140 is in interior region 130, the user may move the side of end effector 108 having legs 110, 112, and 114 toward or against material 140. This may make it easier to prevent material 140 from escaping from interior region 130, due to that side of end effector 108 cupping material 140 with its bowl or scoop shape. Further, with portions of end effector assembly 106 that have greater strut density positioned at the distal end of end effector assembly 106, it is more likely that one or more of the struts will engage material 140. It is contemplated that an area of end effector 108 with less space between adjacent legs/struts may have a greater strut density than an area of end effector 108 with more space between adjacent legs/struts. Additionally or alternatively, it is contemplated that an area of end effector 108 with a greater number of legs/struts may have a greater strut density than an area of end effector 108 with a lesser number of legs/struts.

From the deployed state of end effector 108 in FIG. 1A and/or the capturing state in FIG. 1B, the user may attempt to withdraw material 140 from the subject. The user may move drive members 134 and 136 in the proximal direction at the same time. With this movement, end effector 108 may move towards the stored state. Distal sections 120 of legs 110, 112, 114, and 116 may move closer to each other as proximal sections 122 of legs 110, 112, 114, and 116 are drawn into the distal end of introducer 102. The volume of interior region 130 may decrease.

Eventually, legs 110, 112, 114, and 116 may contact the outer surface of material 140, exerting a grasping force on material 140, and keeping material 140 tight against and/or adjacent to the distal end of introducer 102. At that time, end effector 108 may be in a grasping state, somewhere between the deployed state or capturing state and the stored state. With end effector 108 in the grasping state, the user may pull retrieval device 100 proximally to withdraw it and material 140 from the subject.

During withdrawal of retrieval device 100 and material 140 from the subject, an obstruction may be encountered, halting further withdrawal. For example, if material 140 is large enough that it cannot be withdrawn through an opening or lumen in the subject, material 140 may prevent further withdrawal of retrieval device 100. In order to continue withdrawing retrieval device 100 from the subject, the user may release material 140 from end effector 108.

The user may release material 140 from end effector 108 by moving end effector 108 toward the deployed state. With end effector 108 in the deployed state, withdrawing retrieval device 100 through the obstruction may bring material 140 into engagement with the obstruction, forcing material 140 through one of the gaps between legs 110, 112, 114, and 116, and out of interior region 130.

Additionally or alternatively, the user may move drive member 134 in the distal direction, while keeping drive member 136 still, moving drive member 136 in the distal direction at a slower rate than drive member 134, or moving drive member 134 in the distal direction while moving drive member 136 in the proximal direction. End effector 108 may change shape from the grasping state to the releasing state shown in FIG. 1C. Distal movement of drive member 134 may cause distal movement of the side of end effector 108 having legs 110, 112, and 114 relative to the side of end effector 108 having leg 116. With additional distal movement, and or proximal movement of leg 116, legs 110, 112, and 114 may be drawn to the same side of end effector 108 as leg 116. Drive member 134 may define the distal end of end effector 108. For example, the portion of drive member 134 including coupler 138 may move distally relative to legs 110, 112, 114, and 116, and end cap 118. The portion of drive member 134 may bulge distally beyond end cap 118. An entirety of legs 110, 112, and 114 may be distal to end cap 118.

Moving end effector 108 to the releasing state may increase the volume of interior region 130 from that of the grasping state, allowing material 140 to move more freely. Moving end effector 108 to the releasing state may also move legs 110, 112, 114, and 116 away from material 140. With the portions of end effector 108 that have greater strut density moved away from the distal end of end effector 108, and/or the portions of end effector 108 that have less strut density moved toward the distal end of end effector 108, it may be less likely that one or more struts will engage material 140, allowing material 140 to be released more easily. Moving end effector 108 to the releasing state may also open gaps around drive member 134. Withdrawing retrieval device 100 through the obstruction may bring material 140 into engagement with the obstruction, forcing material 140 through the gaps on either side of drive member 134 and/or coupler 138. The gaps on either side of drive member 134 and/or coupler 138 in the releasing state may be larger than the gaps between legs 110, 112, 114, and 116 when end effector 108 is in the deployed state. With material 140 released, end effector 108 may fit through the obstruction. End effector 108 may also be moved back into the stored state for withdrawal.

There is a possibility that the user may not be able to release material 140 from interior region 130 of end effector 108 even with end effector 108 in the deployed or releasing states. The user may attempt to release material 140 by pulling on a proximal end of drive member 134 or drive member 136. For example, the user may pull on a proximal end of drive member 134. Drive member 136 may have a proximal free end, allowing its free, unobstructed movement distally as drive member 134 is pulled proximally. For example, as the user pulls drive member 134 proximally, drive member 136 may be pulled distally out of the distal end of introducer 102, allowing end effector 108 to be drawn from a position around material 140 into the distal end of introducer 102. All or some of end effector 108 may be stored in introducer 102 in this manner. When all portions of end effector assembly 106 are clear of material 140, retrieval device 100 may be withdrawn from the subject. If material 140 is positioned such that it is engaged by drive member 136 after end effector 108 has been retracted, the user may continue to pull drive member 134 proximally until the free end of drive member 136 exits the distal end of introducer 102, moves around material 140, and enters the distal end of introducer 102, to free retrieval device from material 140. It is contemplated that one of, or both of drive member 134 and drive member 136, may have a proximal free end. Alternatively, a proximal free end may be created by severing a proximal portion of at least one of drive members 134 and 136. For example, the proximal free end may be created by severing a proximal portion of introducer 102 and at least one of the drive members 134 and 136 within the proximal portion. Alternatively, the proximal free end may be created by severing at least one of the drive members 134 and 136 at a location proximal to the proximal end of introducer 102. The proximal location may be at a handle or other suitable actuator (not shown).

Once material 140 has been released, the user may withdraw device 100 from the subject in any suitable manner. For example, the user may continue pulling drive member 134 to withdraw drive member 134, end effector 108, and drive member 136 from the proximal end of introducer 120. Introducer 102 may then be withdrawn. Alternatively, the user may continue pulling drive member 134 until drive member 134, end effector 108, and drive member 136 reside in lumen 104, at which point introducer 120 and its contents may be withdrawn.

Figure 2A:
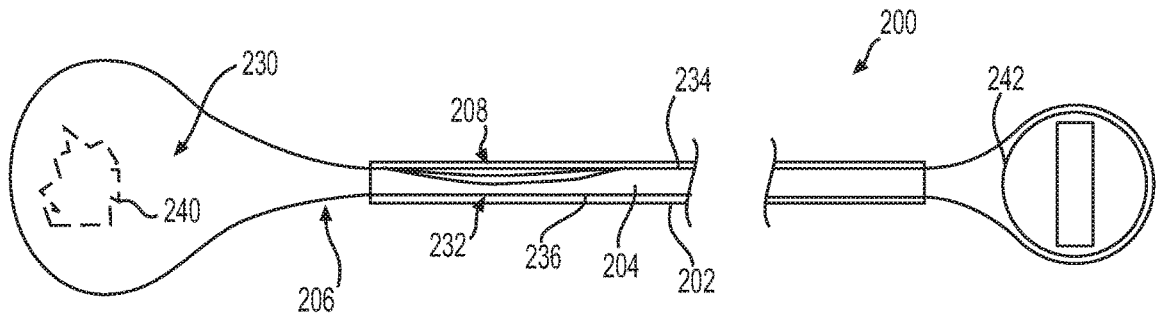
FIG. 2A illustrates portions of an exemplary retrieval device, with an end effector assembly of the device in an initially-deployed state, according to an aspect of the present disclosure.
Figure 2B:
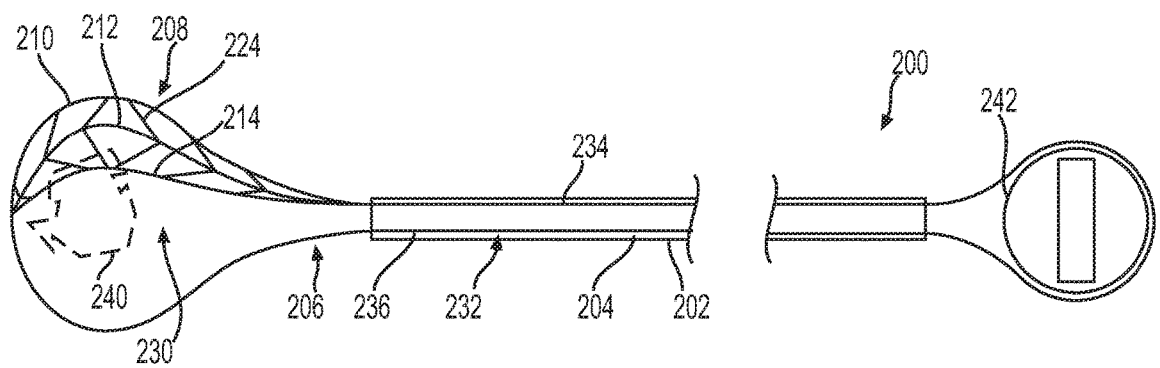
FIG. 2B illustrates portions of the retrieval device of FIG. 2A, with the end effector of the end effector assembly in a partially-deployed state, according to an aspect of the present disclosure.
Figure 2C:
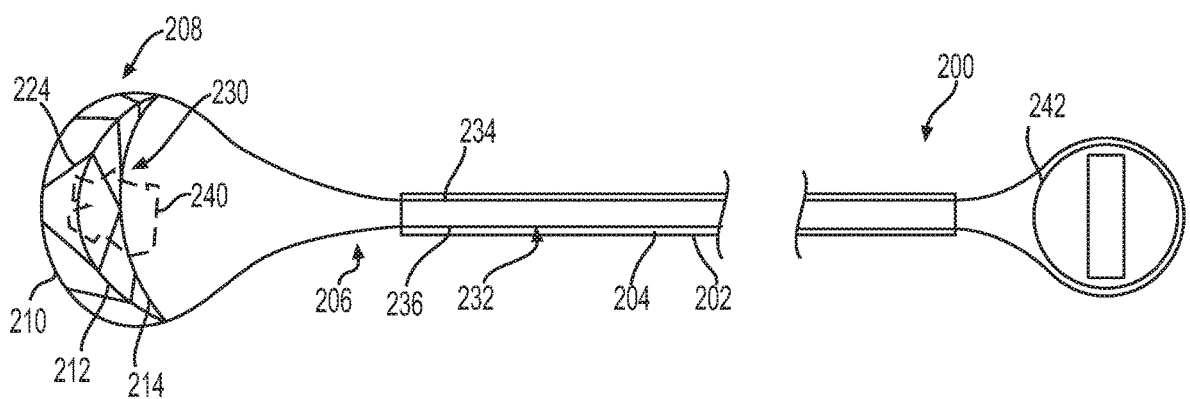
FIG. 2C illustrates portions of the retrieval device of FIG. 2A, with the end effector in a fully-deployed state, according to an aspect of the present disclosure.

FIGS. 2A-2C illustrate an exemplary retrieval device 200. Retrieval device 200 may include an introducer 202, such as a sheath or catheter made of a flexible material. Introducer 202 may include a lumen 204. It is also contemplated that introducer 202 may include a plurality of longitudinally-extending and/or parallel lumens. An end effector assembly 206 may be received in lumen 204. End effector assembly 206 may include an end effector 208 for capturing material. End effector 208 may include a plurality of legs 210, 212, and 214 (FIG. 2B). One or more of the legs 210, 212, and 214 may extend in a longitudinal direction. End effector 208 may also include a plurality of legs 224. One or more of legs 224 may extend between pairs of legs 210, 212, and 214. One or more of legs 224 may extend in an angled or transverse direction relative to one or more of legs 210, 212, and 214. It should be understood that any suitable number of legs may be used. Legs 210, 212, 214, and 224 may be deployed to form a net, cage, or web for grasping material 240.

Opposite ends of end effector 208 (and particularly legs 210, 212, and 214) may be coupled to ends of drive members 234 and 236, which may form part of a drive member assembly 232. For example, ends of legs 210, 212, and 214 may be welded or soldered to the ends of drive members 234 and 236, joined by a crimp tube (not shown), and/or attached by any other suitable attachment mechanism. The joint between ends of legs 210, 212, and 214, and ends of drive members 234 and 236, may be located where legs 210, 212, and 214 meet.

Drive members 234 and 236 may be two portions of a single elongated member, such that end effector 208 and drive members 234 and 236 form a continuous loop. An actuator 242 of the drive member assembly may engage a proximal end of the continuous loop. Actuator 242 may include a rotatable knob, a gear mechanism, and/or any other suitable actuator. As actuator 242 rotates, it may rotate the continuous loop. In an alternative arrangement, actuator 242 may be coupled to ends of drive members 234 and 236, such that end effector 208, drive members 234 and 236, and actuator 242 form the continuous loop. Actuator 242 may be used in retrieval device 100. For example, proximal portions of drive members 134 and 136 may be operatively coupled to actuator 242, such that movement of actuator 242 may extend and retract end effector 108, and rotation of actuator 242 may change the shape of end effector 108.

Drive members 234 and 236 may be moved at the same time. Drive members 234 and 236 may be moved in the same direction. For example actuator 242 may be movable proximally relative to introducer 202 to move both drive members 234 and 236 proximally, bringing the distal end of end effector assembly 206 into the stored state within introducer 202. Actuator 242 may be movable distally relative to introducer 202 to move drive members 234 and 236 distally, thus moving the distal end of end effector assembly 206 into the deployed state beyond the distal end of introducer 202. Drive members 234 and 236 may also be moved in different directions. For example, actuator 242 may be rotated in a clockwise direction to move drive member 234 proximally and drive member 236 distally. Actuator 242 may be rotated in a counterclockwise direction to move drive member 234 distally and drive member 236 proximally. Any combination of the above movements may be executed by a user to perform a procedure. While drive members 234 and 236 are shown as extending through lumen 204, it should be understood that each of drive members 234 and 236 may extend through its own individual lumen when introducer 202 includes a plurality of lumens.

As shown in FIG. 2A, actuator 242 has been rotated to a position where the distal end of end effector assembly 206 is defined by a portion of drive member 236. Actuator 242 has been moved distally relative to introducer 202 to a position where the distal end of end effector assembly 206 is deployed. In this initially deployed state, the portion of drive member 236 extends out of the distal end of introducer 202, and expands. The extended portion of drive member 236 forms a loop. The loop may be positioned around material 240 by the user, such that material 240 is within an interior region 230. The loop may define a path around material 240. End effector 208 may follow that path during deployment. In the initially deployed state of end effector assembly 206, end effector 208 may be stored in lumen 204 of introducer 202. End effector 208 may be contracted with legs 210, 212, and 214 adjacent each other or in contact, with little or no gaps between them.

From the initially deployed state, the user may rotate actuator 242 in the counterclockwise direction to move drive member 234 distally and drive member 236 proximally. The counterclockwise rotation may partially deploy end effector 208 from the distal end of introducer 202, while moving part of drive member 236 back into introducer 202 (FIG. 2B). End effector 208 may be guided around a side of material 240. End effector 208 may form a bowl or scoop shape, cupping material 240. The region of end effector assembly 206 with the greatest density of struts may be at a side of end effector assembly 206. It is contemplated that an area of end effector 208 with less distance between adjacent struts may have a greater density of struts than an area of end effector 208 with greater distance between adjacent struts. Additionally or alternatively, it is contemplated that an area of end effector 208 with a greater number of struts may have a greater density of struts than an area of end effector 208 with a lesser number of struts.

From the partially deployed state, further counterclockwise rotation of actuator 242 may move end effector 208 into the fully deployed state shown in FIG. 2C. In the fully deployed state, end effector 208 may form the distal end of end effector assembly 206, and may be bowl or scoop shaped to cup material 240. Material 240 may be at least partially contained within the interior region 230 defined by end effector 208. The region of end effector assembly 206 with the greatest density of struts may be at the distal end of end effector assembly 206.

End effector 208 may expand as it moves to the partially and fully deployed states. For example, legs 210, 212, 214, and 224 may spread away from each other. Legs 210, 212, 214, and 224 may define an interior region 230 for receiving material, such as material 240. Legs 210, 212, 214, and 224 may be formed of any suitable material including, but not limited to, metals, polymers, or a combination of materials. For example, one or more of legs 210, 212, 214, and 224 may be formed with a shape memory material, such as Nitinol or stainless steel, and may be treated to possess an internal bias causing one or more of legs 210, 212, 214, and 224 to spread outwardly in the absence of a constraining force.

When in the fully deployed state, with material 240 captured, the user may prepare to withdraw material 240 from the subject. The user may move drive members 234 and 236 in the proximal direction at the same time by moving actuator 242 proximally relative to introducer 202. End effector 208 may move towards the stored state. Legs 210, 212, 214, and 224 may be drawn into the distal end of introducer 202. The volume of interior region 230 may decrease. Eventually, legs 210, 212, 214, and 224 may contact the outer surface of material 240, exerting a grasping force on material 240, and keeping material 240 tight against and/or adjacent to the distal end of introducer 202. At that time, end effector 208 may be in a grasping state. With distal end effector 208 in the grasping state, the user may pull retrieval device 200 proximally to withdraw it and material 240 from the subject.

During withdrawal of retrieval device 200 and material 240 from the subject, an obstruction may be encountered, and withdrawal may be halted. For example, if material 240 is large enough that it cannot fit through an opening or lumen in the subject, engagement between material 240 and the obstruction may prevent further withdrawal of retrieval device 200. In order to continue withdrawing retrieval device 200 from the subject, the user may release material 240 by moving end effector 208 toward the partially deployed state, or to the initially deployed state. With distal end effector 208 in the partially deployed state (FIG. 2B), withdrawing retrieval device 200 through the obstruction may bring material 240 into engagement with the obstruction, forcing material 240 out of interior region 230 through gaps formed between the extended portion of drive member 236 and legs 210 and 214 of end effector 208. With distal end effector 208 in the initially deployed state (FIG. 2A), material 240 may be forced out of interior region 230 at either side of the extended portion of drive member 236. Once material 240 has been released, the user may withdraw retrieval device 200 in any suitable manner, without being blocked by the obstruction.

There is a possibility that the user may not be able to release material 240 from interior region 230 by moving end effector 208 into the partially deployed or initially deployed states. To facilitate release of material 240 and removal of retrieval device 200, the user may sever at least one of drive members 234 and 236 at the proximal end of end effector assembly 206. The user may pull on one of drive members 234 and 236. For example, the user may pull on drive member 234. End effector 208 may be drawn into the distal end of introducer 202, making it easier to release material 240. The extended portion of drive member 236 may be drawn out from the distal end of introducer 202 to facilitate proximal movement of end effector 208. The severed end of drive member 236 may be drawn into the proximal end of introducer 202. Continued pulling may draw drive member 236 distally through lumen 204, out the distal end of lumen 204, around material 240, back into the distal end of lumen 204, and out of the proximal end of introducer 202. With material 240 released from end effector assembly 206, the user may withdraw device 200 from the subject in any suitable manner.

A method of using the retrieval device 100 or 200 will now be described. The retrieval device 100 or 200 may be readied for use by ensuring that the end effector assembly 106 or 206 is in the stored state within the lumen 104 or 204 of the introducer 102 or 202. For retrieval device 100, end cap 118 may remain outside of introducer 102.

The user may insert an endoscope (not shown), having one or more lumens and a distal imaging device, into a subject through a natural body orifice or an incision. The user may navigate the endoscope through the subject's anatomy until the distal end of the endoscope is in the desired position.

The user may insert the retrieval device 100 or 200 into the endoscope, and move the retrieval device 100 or 200 through a lumen of the endoscope. A distal portion of the retrieval device 100 or 200 may extend out of a distal end of the endoscope. The distal portion of the retrieval device 100 or 200 may be positioned near the material 140 or 240 the user wants to remove from the subject.

The user may deploy the distal end of the end effector assembly 106 or 206 for capturing the material 140 or 240. For example, end effector 108 may be deployed from the distal end of introducer 102 to try to capture material 140 (FIG. 1A). The user may maneuver end effector 108 to position material 140 in interior region 130. As another example, a loop portion of drive member 236 may be deployed from the distal end of introducer 202 and positioned around material 240 (FIG. 2A), and then distal end effector 208 may be deployed along the path defined by the loop portion (FIG. 2B).

In order to get the material 140 or 240 into the interior region 130 or 230, the user may move the end effector 108 or 208 into the capturing state of FIG. 1B or FIG. 2C. The portion of the end effector 108 or 208 having the greatest strut density may form the distal end of the end effector assembly 106 or 206, also helping capture the material 140 or 240.

When the material 140 or 240 is in the interior region 130 or 230, and possibly engaged by one or more of the legs 110, 112, 114, and 116 or 210, 212, 214, and 224, the user may move the end effector 108 or 208 into the grasping state. The legs 110, 112, 114, and 116 or 210, 212, 214, and 224 may close around the material 140 or 240. The legs 110, 112, 114, and 116 or 210, 212, 214, and 224 may contact the outer surface of the material 140 or 240, and may hold the material 140 or 240 adjacent the distal end of the introducer 102 or 202.

The user may pull the retrieval device 100 or 200 proximally out of subject to remove the material 140 or 240 from the subject. During withdrawal, the material 140 or 240 may encounter an obstruction, preventing full withdrawal of the retrieval device 100 or 200 and the material 140 or 240 from the subject. In order to remove the retrieval device 100 or 200 from the subject, the user may release the material 140 or 240 from the end effector 108 or 208. The user may facilitate release of the material 140 or 240 by moving end effector 108 or 208 back into the deployed state shown in FIG. 1A, into the release state shown in FIG. 1C, into a release state similar to that shown in FIG. 1C except with the distal end of end effector assembly 106 being formed by a portion of drive member 136 rather than drive member 134, into the partially deployed state shown in FIG. 2B, or into the initially deployed state shown in FIG. 2A. The strut density of the distal end of the end effector assembly 106 or 206 may decrease, making it easier for the material 140 or 240 to move out of the interior region 130 or 230 as the retrieval device 100 or 200 is withdrawn in the proximal direction.

Additionally or alternatively, the user may pull on the proximal end of the drive member 134 or 234 to draw the end effector 108 or 208 into the distal end of the introducer 102 or 202. The drive member 136 or 236 may be drawn distally through the introducer 104 or 204 to allow retraction of end effector 108 or 208. With additional pulling, all of end effector assembly 106 or 206 may be moved out of contact with material 140 or 140. It is contemplated that the entire end effector assembly 106 or 206 may be withdrawn from the proximal end of the introducer 102 or 202. The rest of the retrieval device 100 or 200 may be removed from the subject. The material 140 or 240 may be left in the subject.

The disclosed retrieval devices and methods may be utilized in any suitable application involving the capture and removal of material from the body. Any aspect set forth herein may be used with any other aspect set forth herein. The devices may be used in any suitable medical procedure, may be advanced through any suitable body lumen and body cavity, and may be used to remove material from any suitable body portion. For example, the devices described herein may be used through any natural body lumen or tract, including those accessed orally, vaginally, rectally, nasally, urethrally, or through incisions in any suitable tissue.

It will be apparent to those skilled in the art that various modifications and variations can be made in the disclosed retrieval devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A retrieval device, comprising:
a sheath;
a drive member assembly comprising:
a first drive member in the sheath, and
a second drive member in the sheath, the first drive member being movable relative to the second drive member; and
an end effector coupled to the first and second drive members, the end effector comprising a plurality of legs, the drive member assembly and the plurality of legs forming a loop, wherein one of the first or second drive members is configured to form a distal portion of the loop, the distal portion being extendable out of the sheath while the plurality of legs are contained in the sheath.

2. The retrieval device of claim 1, wherein the first and second drive members and the end effector form a continuous loop.

3. The retrieval device of claim 1, wherein the drive member assembly comprises an actuator coupled to the first and second drive members.

4. The retrieval device of claim 3, wherein the actuator is configured to rotate to move one of the first or second drive members relative to the other of the first or second drive members.

5. The retrieval device of claim 3, wherein the actuator is configured to move in one of a proximal direction to simultaneously move the first and second drive members in the proximal direction, or the actuator is configured to move in a distal direction to simultaneously move the first and second drive members in the distal direction.

6. The retrieval device of claim 3, wherein the actuator includes a rotatable knob or a gear.

7. The retrieval device of claim 1, wherein moving the first drive member relative to the second drive member extends the end effector out of the sheath.

8. The retrieval device of claim 1, wherein, in an initial configuration, an entirety of the end effector is contained within the sheath.

9. The retrieval device of claim 1, wherein:
in a first configuration, a portion of the first drive member is configured to be a distalmost portion of the loop; and
in a second configuration, a portion of the end effector is configured to be the distalmost portion of the loop.

10. The retrieval device of claim 1, wherein the plurality of legs includes a first leg, a second leg, and a third leg, wherein:
first ends of each of the first leg, the second leg, and the third leg, are directly coupled to the first drive member; and
second ends of each of the first leg, the second leg, and the third leg, are directly coupled to the second drive member.

11. The retrieval device of claim 10, wherein the plurality of legs also includes:
one or more fourth legs extending transversely between the first leg and the second leg; and
one or more fifth legs extending transversely between the second leg and the third leg.

12. The retrieval device of claim 11, wherein the first and second drive members and the end effector form a continuous loop.

13. The retrieval device of claim 12, wherein:
in a first configuration, a portion of the first drive member is configured to be a distalmost portion of the loop; and
in a second configuration, a portion of the end effector is configured to be the distalmost portion of the loop.

14. The retrieval device of claim 13, wherein, in a third configuration, a portion of the second drive member is configured to be a distalmost portion of the loop.

15. The retrieval device of claim 10, wherein the first leg, the second leg, and the third leg each includes a shape memory material, and the first leg, the second leg, and the third leg are treated to have an internal bias causing the first leg, the second leg, and the third leg to move away from one another, absent a constraining force.

16. A retrieval device, comprising: a first wire portion; an end effector coupled to the first wire portion, the end effector comprising a plurality of legs; and a second wire portion coupled to the end effector, wherein the retrieval device is movable between a first configuration, a second configuration, and a third configuration, wherein: in the first configuration, the first wire portion is disposed further from a proximal end of the retrieval device than both the end effector and the second wire; in the second configuration, the end effector is disposed further from the proximal end than both the first wire portion and the second wire portion; and in the third configuration, the second wire portion is disposed further from the proximal end than both the first wire portion and the end effector.

17. The retrieval device of claim 16, wherein the first wire portion, the second wire portion, and the end effector form a continuous loop.

18. A retrieval device, comprising:
a sheath;
a first drive member in the sheath;
a second drive member in the sheath, the second drive member being movable relative to the first drive member; and
an end effector retractable into and extendable out of the sheath, the end effector extending from a first end toward a second end, the end effector including a plurality of legs:
wherein the end effector is configured such that movement of the first drive member in the sheath moves the end effector between:
a first position, in which the first end is a distalmost portion of the end effector and the second end is a proximalmost portion of the end effector, and
a second position, in which the second end is the distalmost portion of the end effector and the first end is the proximalmost portion of the end effector.

19. The retrieval device of claim 18, wherein the first and second drive members and the end effector form a continuous loop.

20. The retrieval device of claim 18, wherein the plurality of legs includes a first leg, a second leg, and a third leg, wherein: first ends of each of the first leg, the second leg, and the third leg, are directly coupled to the first drive member; and second ends of each of the first leg, the second leg, and the third leg, are directly coupled to the second drive member.

* * * * *